United States Patent [19]

Ammerman

[11] Patent Number: 4,669,106
[45] Date of Patent: May 26, 1987

[54] APPARATUS FOR AIDING IN CERVICAL SPINE RADIOGRAPHIC PRODUCTION

[76] Inventor: Stephen W. Ammerman, 370 Lower Lake Rd., Lake Sherwood, Calif. 91361

[21] Appl. No.: 714,959

[22] Filed: Mar. 25, 1985

[51] Int. Cl.[4] .............................................. A61B 6/04
[52] U.S. Cl. .................................. 378/208; 128/133; 269/328
[58] Field of Search ................ 378/20, 177, 180, 195, 378/208, 209; 5/82 R; 128/75, 78, 133, 134; 269/328

[56] References Cited

U.S. PATENT DOCUMENTS

| | | | |
|---|---|---|---|
| 1,115,794 | 11/1914 | Eriksen | 269/328 |
| 1,562,150 | 11/1925 | Denton | 5/82 R |
| 1,622,313 | 3/1927 | Gellhorn | 269/328 |
| 1,968,120 | 7/1934 | Barghausen et al. | 269/328 |
| 3,025,397 | 3/1962 | Travis et al. | 378/208 |
| 3,596,655 | 8/1971 | Corcoran | 128/75 |
| 3,629,581 | 12/1971 | Smith | 378/209 X |
| 4,127,120 | 11/1978 | Applegate | 128/134 |
| 4,383,524 | 5/1983 | Boger | 128/75 |

FOREIGN PATENT DOCUMENTS 961208 6/1964 United Kingdom ............... 128/134

Primary Examiner—Frederick R. Schmidt
Assistant Examiner—Steven P. Schad
Attorney, Agent, or Firm—Jack C. Munro

[57] ABSTRACT

An apparatus for repositioning (by depressing) shoulders of a prone patient at a displaced position to facilitate the obtaining of an unobstructive lateral radiograph (X-ray) of all seven (in number) vertebrae of the cervical section of the spine. The apparatus of the present invention utilizes an elongated substantially planar board upon which the patient is to be located in a prone position. A perineal post is mounted on the board and is to contact the patient at the perineal area, basically immobilizing the torso of the patient. A movable plate is mounted on the upper end of the board which includes a pair of bracket assemblies which are to be in contact with the shoulders of the patient. The plate includes a manually operated winch assembly which when operated applies pressure against the shoulders of the patient moving such to a displaced position to thereby facilitate the taking of the lateral radiograph of the cervical section of the spine.

12 Claims, 10 Drawing Figures

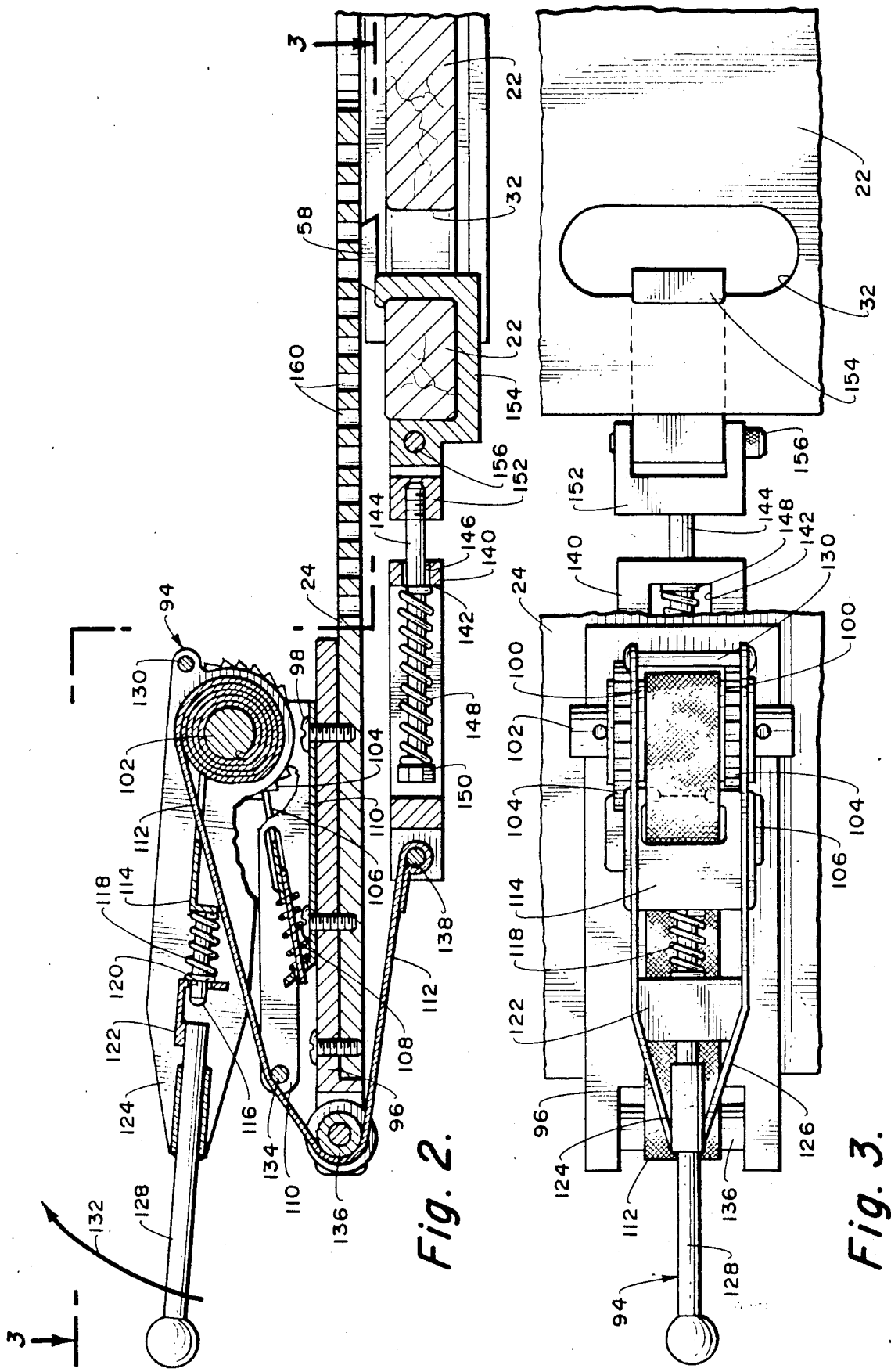

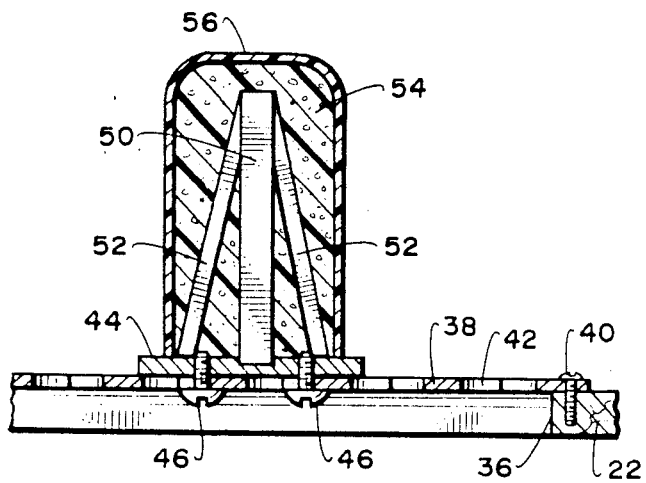
Fig. 8.
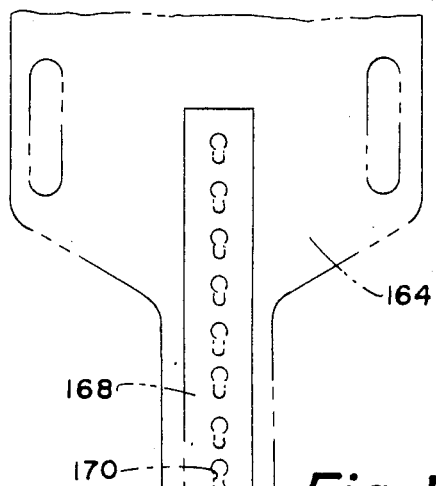
Fig. 10.
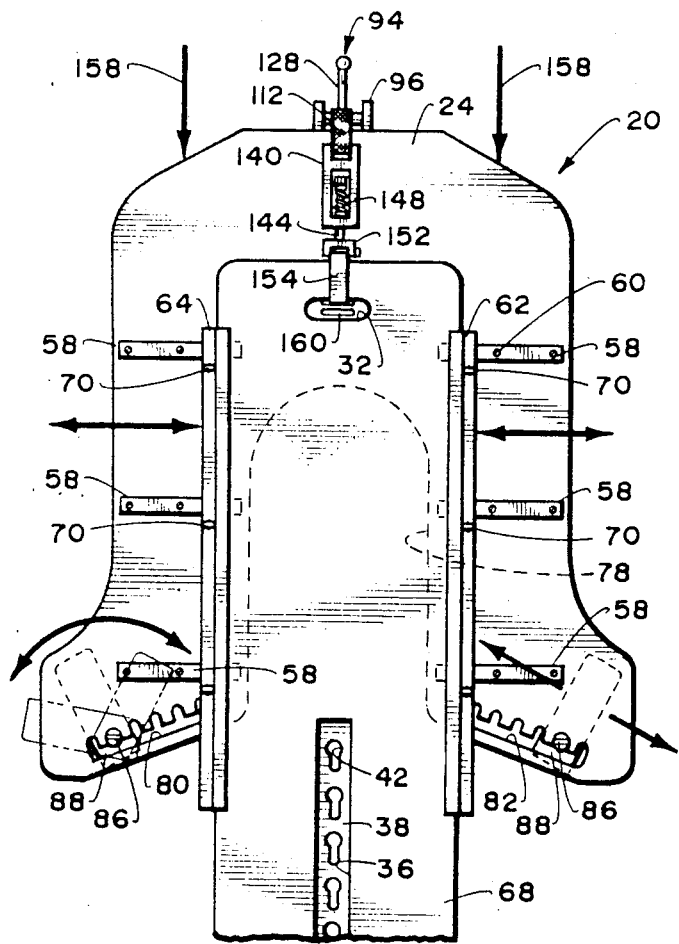
Fig. 9.
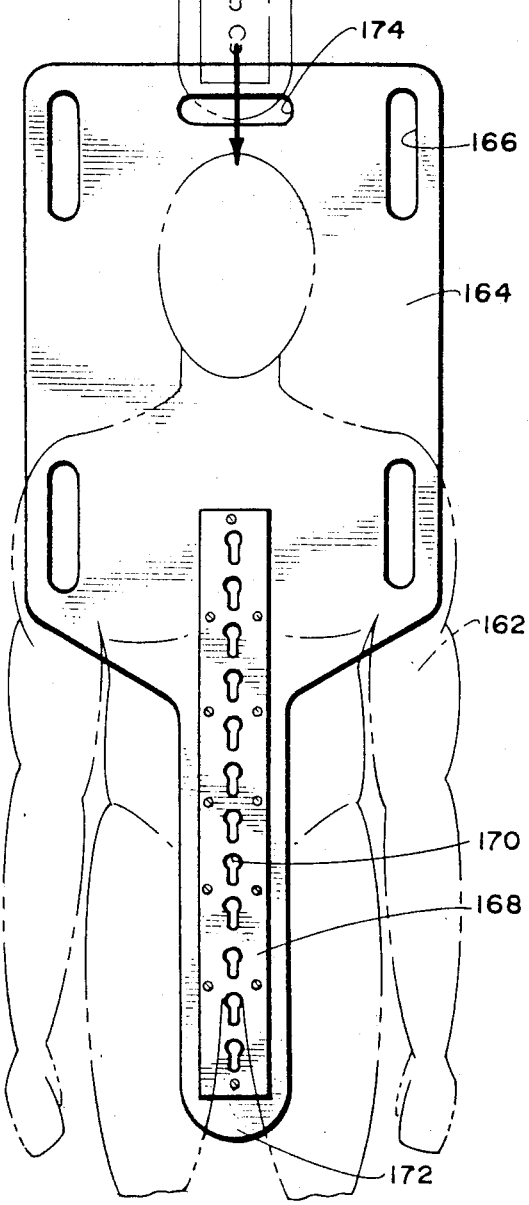

APPARATUS FOR AIDING IN CERVICAL SPINE RADIOGRAPHIC PRODUCTION

BACKGROUND OF THE INVENTION

The field of this invention relates to a positioning apparatus for positioning a patient undergoing X-ray examination of the cervical portion of the spine in order to obtain an unobstructed lateral X-ray of the cervical spine.

In dealing with any accident patient, especially anyone who is unconscious, there is always a definite concern that the patient may have a spinal injury, such as a broken back. Moving of any such patient may further aggravate the injured back and possibly even may cause paralysis or death.

Within the emergency medical field it is common to utilize at the scene of an accident a board upon which the patient is placed in a prone position. The board is what is commonly referred to as a "spine board". The patient is positioned with the patient's back in direct contact with the board. The patient and board are then transported to the emergency room of a hospital.

Every traumatized patient who enters the emergency room of a hospital is under "C-spine precautions". This means that before further diagnostic tests can begin, the emergency physician must visualize the cervical spinal vertebrae radiographically. Radiographic observation of the cervical section of the spine must be accomplished laterally, that is, from the side of the patient. The X-ray beam must pass unobstructed in a perpendicular relationship to the cervical vertebrae in order to obtain an adequate X-ray. If an adequate cross table lateral X-ray of the sixth and seventh vertebrae is not obtained at this time, there is a tremendous potential morbidity involved.

Accurate lateral radiographs of the cervical vertebrae are difficult to obtain because of the interference from the shoulders of the patient. The shoulders naturally block the view of part of the sixth and all of the seventh vertebrae. Therefore, with a patient occupying a normal at rest position, the shoulders prevent radiograph observation of a part of the sixth and all of the seventh vertebrae which will allow injury to these two vertebrae to go undetected. Movement of the patient and injury to either one of these vertebrae could result to obligating that patient to life in a wheelchair.

The normal procedure currently in use in emergency rooms is the archaic method of physically pulling by an X-ray technician on the patient's arms in order to displace the shoulders sufficiently downward so that the X-ray beam is hopefully not obstructed in obtaining a radiograph of the C6 and C7 vertebrae. The disadvantage of this method is that displacement of the shoulder by the technician is not adequate to clear the view of the entire cervical area. Also, this requires that the technician remain in the radiographic room during the X-ray exposure which undesirably risks the technician to radiation.

Previously there have been attempts of constructing a board which facilitates the obtaining of a single satisfactory radiograph exposure of the C6 and C7 vertebrae of a traumatized human being. Examples of such previous devices are shown within U.S. Pat. Nos. 3,629,581, 4,127,120 and 4,383,524. Each of these prior art devices utilize a series of straps which are to be attached to the arms of the patient and the straps utilized in conjunction with the legs of the patient to exert a force in a downward direction on the arms to pull the shoulders sufficiently to facilitate the taking of the necessary X-ray. Installation of any one of these prior art devices is complicated and time consuming. Also, if the patient is unconscious any strap-type device may be ineffective.

There is a need to construct a device that will aid a physician to quickly obtain a single cervical radiograph of any patient, whether conscious or unconscious, which can be quickly and easily installed in conjunction with the patient by individuals of minimum skill.

SUMMARY OF THE INVENTION

The apparatus of the present invention utilizes an elongated spine board which is basically conventional with the exception that the spine board is modified to include a series of keyhole slot arrangements longitudinally disposed along the elongated axis of the board. A perineal post assembly is to be engageable with any directly adjacent pair of keyhole slots with the pair of used keyhole slots being selected according to the size of the individual placed on the board so that the post will be in direct contact with the perineal section of the patient. A plate is then slidingly engaged with the upper end of the board (about the head of the patient) by means of a pair of parallel rails mounted on the undersurface of the plate. One rail engages one side edge of the board while the other rail engages the opposite side edge of the board. These rails are to be adjustable to vary the spacing between the rails so as to have the plate accommodate to different width boards. Mounted on the upper surface of the plate are a pair of spaced apart shoulder contacting brackets. Each bracket is mounted within an elongated slot and each bracket can occupy any one of several different positions within each slot so that the brackets can be adjusted to accommodate to the shoulder width of the patient. Mounted on the upper surface of the plate is a winch assembly. The winch assembly is to be manually operated to effect tightening of a strap. The strap is connected to a spring assembly located directly adjacent the undersurface of the plate. The free end of the spring assembly is connected to the board. As the winch is operated, force is applied to both shoulders of the patient and stretching of the spring is to be observable through a plurality of spaced apart apertures within the plate. The extent of the stretching of the spring gives an indication to the operator of the amount of force that is being applied to the patient to eliminate the possibility of over application of force.

The primary objective of the present invention is to construct an apparatus which can be quickly and easily installed in conjunction with a patient in order to obtain the needed radiograph of the C6 and C7 vertabrae. Previously, medical legal liability has historically required numerous X-rays and even then, oftentimes inadequate X-rays of the C7 vertebra is obtained. This inadequacy results, at times, in catastrophic personnel and hospital injury litigation. Using the apparatus of the present invention, an X-ray of the entire cervical region of a patient can be obtained by the taking of a single radiograph rather than the multitudes that were previously taken. An additional advantage of the present invention is that by decreasing the number of X-rays being exposed, both the patient and the medical personnel are spared unneeded excessive radiation exposure.

Another advantage of the present invention is that the time interval that has elapsed from the initiation of the process to obtain the cervical radiograph is significantly shortened, therefore, providing significant cost effective savings by decreasing the time hospital personnel must be utilized.

The physician is not able to proceed diagnostically, or move the patient, until adequate C7 confirmation has been met. Another objective of the present invention is that the precious loss of critical time is significantly decreased, thereby, minimizing the compromising of the traumatized patient.

BRIEF DESCRIPTION OF THE DRAWINGS

FIG. 2 is a longitudinal, cross-sectional view through the winch assembly utilized to apply a force to move a plate mounted on the board in a unidirectional manner taken along line 2—2 of FIG. 1;

FIG. 3 is a top plan view of the winch assembly taken along line 3—3 of FIG. 2;

FIG. 8 is a cross sectional view through the perineal post utilized in conjunction with this invention taken along line 8—8 of FIG. 1;

FIG. 9 is a bottom plan view similar to FIG. 4 but showing the board in solid lines and showing the plate in position to be mounted on a board which is substantially more narrow than the board shown in FIG. 4; and FIG. 10 is a top plan view showing a modified version of the board of the present invention which is designed to be utilized to be slipped under a patient if the patient has not already been located on a board similar to that shown within FIG. 1.

DETAILED DESCRIPTION OF THE SHOWN EMBODIMENT

Figure 1:
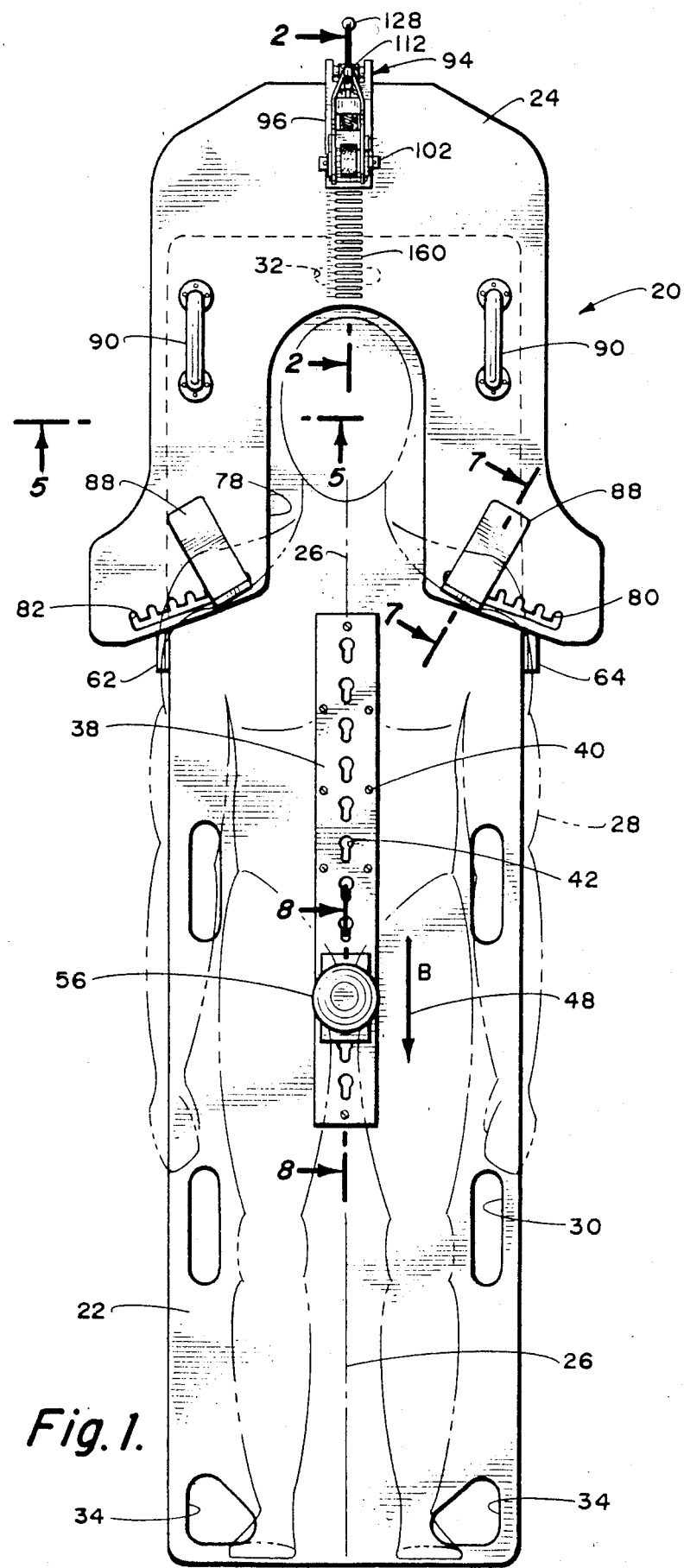
FIG. 1 is a top plan view of the body positioning apparatus of the present invention depicting a patient, in phantom, in a prone position on the upper surface of the board.

Referring particularly to the drawings, there is shown the apparatus 20 of the present invention which is composed generally of a spine board 22 and a plate 24. The board 22 is basically conventional and usually will be constructed of rigid material such as wood. Board 22 has an elongated center axis 26 upon which the patient 28 is to be placed in a prone position. When the patient 28 is so positioned, the spine (not shown) of the patient 28 is in substantial alignment with the longitudinal center axis 26.

The board 22 has formed therein directly adjacent each side edge thereof a plurality of spaced apart elongated openings 30. The openings 30 are to function as handholes to facilitate the picking up and carrying of the board 22. A similar opening 32 is formed within the upper end of the board 22. Within the lower end of the board 22 there is formed a pair of spaced apart triangularly shaped handhole openings 34. The use of openings 30, 32 and 34 are deemed to be conventional within spine boards.

The spine board 22 is different from the conventional spine board in that it has an elongated opening 36 formed within the center of the board 22 in substantial alignment with the elongated center axis 26. This elongated opening 36 is then covered on the upper surface of the board 22 by means of a strip plate 38. The strip plate is fixedly mounted to the board 22 by means of a plurality of conventional screw fasteners 40. The strip plate 38 also includes a plurality of keyhole slots 42. Each of the keyhole slots 42 are basically identical and are evenly spaced apart along the elongated center axis 26. It is to be known that there are twelve in number of the keyhole slots 42 shown. The actual number and the spacing between the keyhole slots 42 is deemed to be a matter of choice.

A mounting plate 44 has mounted on its undersurface a pair of enlarged head threaded fasteners 46. One of the threaded fasteners 46 is to engage with one keyhole slot 42 with the other threaded fastener 46 to engage with another keyhole slot 42. The keyhold slots 42 are positioned such that downward pressure in the direction of arrow 48 securely holds in position the mounting plate 44 in conjunction with the two in number of the keyhole slots 42 that it is connected with. It is to be understood that the mounting plate 44 can be moved to occupy any two directly adjacent keyhole slots 42. Disengagement of the mounting plate occurs by movement of same in the direction opposite to the arrow 48 which will then permit the enlarged headed fasteners 46 to be disengaged from the enlarged sections of each of the keyhole slots 42.

Fixedly mounted on the mounting plate 44 and extending therefrom is a center post 50. Welded to the center post 50 on each longitudinal side thereof (along axis 26) are a pair of braces 52. The post 50 and the braces 52 are completely encased with a cushioning material 54 forming a substantially cylindrical shape. Cushioning material 54 is then covered with a plastic covering material 56. The mounting plate 44, the fasteners 46, the center post 50, the braces 52, cushioning material 54 and the cover 56 all constitute a perineal post assembly. This perineal post assembly is to be selectively positioned on the strip plate 38 so that the cover 56 will be in direct contact with the perineal section of the crotch of the patient 28. It is the function of this post to prevent movement of the patient 28 in the direction of the arrow 48.

Mounted on the undersurface of the plate 24 are a series of laterally directed mounting rails 58. These rails 58 (shown to be six in number) are each fixedly mounted on the plate 24 by means of screw fasteners 60. Each of the mounting rails 58 are located in a parallel relationship with respect to each other and are of the same length. It is to be noted that there are three in number of the rails 58 located on one side of the mounting plate 24 with three in number of the rails 58 located on the opposite side of the plate 24.

Connecting the mounting rails 58 on one side is a side rail 62. A similar side rail 64 is mounted on the mounting rails 58 located on the opposite side of the plate 24. The side rails 62 and 64 are located in a parallel spaced apart relationship. Each of the side rails 62 and 64 include a series of dovetail slots 66. Each of the rails 58 is of a dovetail configuration which is capable of mating within one of the dovetail slots 66. As a result, each of the rails 62 and 64 are held in contact with their respective rails 58 but are slidable therealong in a direction toward and away from the elongated center axis 26.

Figure 4:
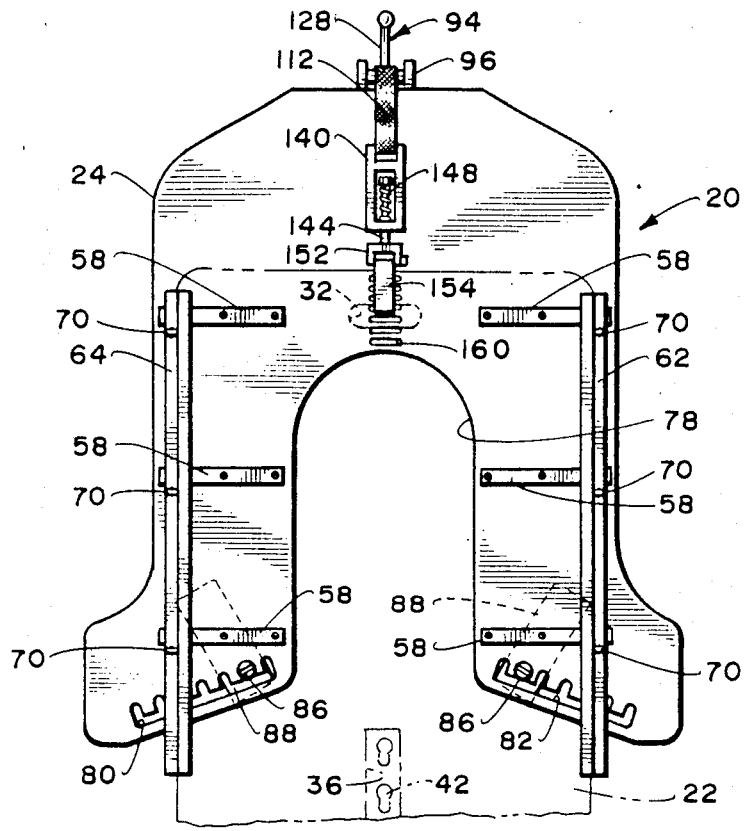
FIG. 4 is a bottom plan view of the plate utilized in conjunction with the board showing the board in phantom.
Figure 5:
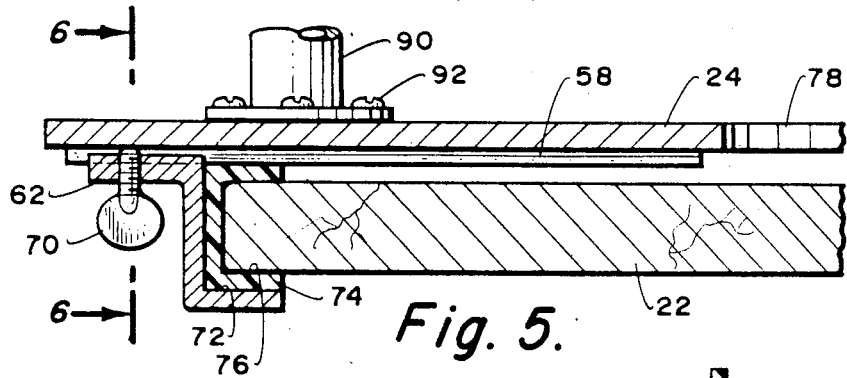
FIG. 5 is a cross-sectional view through a portion of the board and the plate showing the lateral adjustment structure utilized in conjunction with the rails mounted on the undersurface of the plate for the purpose of sliding the plate on the board.
Figures 6, 7:
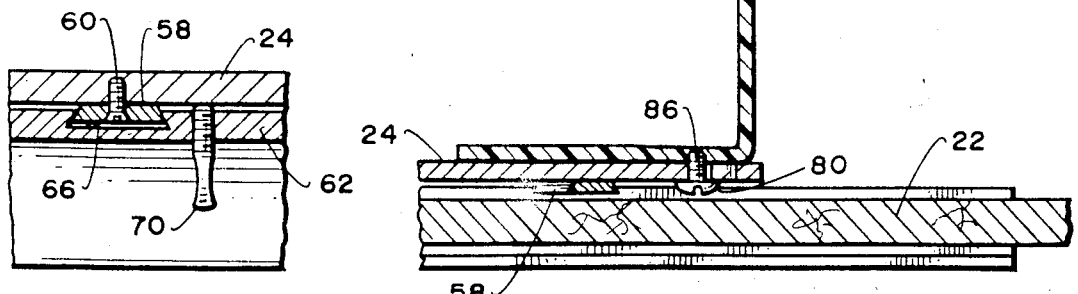
FIG. 6 is a cross sectional view taken along line 6—6 of FIG. 5.
FIG. 7 is a cross sectional view taken along line 7—7 of FIG. 1 showing in more detail the shoulder contacting bracket utilized in conjunction with the structure of this invention.

The amount of sliding movement of each of the rails 62 and 64 has been preselected to be about five inches in length. This means that the total spacing between the rails 62 and 64 may vary as much as ten inches. Therefore, if the minimum spacing between the rails 62 and 64, shown in FIG. 9 of the drawings, is twelve inches, then the side rails 62 and 64 can be adjusted to its furthest out position shown in FIG. 4 of the drawings to accommodate a twenty-two inch board 22. The board 68 in FIG. 9 is twelve inches wide. Each of the rails 62 and 64 can be fixed in its established position by means of one or more thumb screws 70. Each of the rails 62 and 64 include a channel shaped area 72.

Fixedly mounted to each of the rails 62 and 64 within the channel shaped area 72 is a plastic elongated, U-shaped in cross section, guide strip 74. Each guide strip 74 includes an interior elongated recess 76. An edge of the board 22 is to be located within one of the recesses 76 with the opposite edge of the board 22 to be located in the other recess 76. It is to be understood that each of the guide rails 62 and 64 are capable of free sliding movement on the board 22 in the direction along the elongated center axis 26.

Formed within the plate 24 is an enlarged U-shaped recess 78. The recess 78 is open at the front most edge of the plate 24. It is to be noted that rail 62 is located on one side of the recess 78 with the rail 64 being located on the opposite side of the recess 78. The function of the recess 78 is to provide an area of accommodation for the head of the patient 28.

Formed within the plate 24 directly adjacent the uppermost edge thereof on one side of the recess 78 is an elongated slot 80. A similar slot 82 is formed within the plate 24 on the opposite side of the recess 78. Each of the slots 80 and 82 have a plurality of notches formed therein. Each notch to be connectable with an enlarged fastener 86. Each fastener 86 is threadibly secured to an L-shaped bracket 88. The brackets 88 are identical in construction. The brackets 88 will normally be constructed of a rigid material such as plastic, metal or the like.

It is to be understood that either of the brackets 88 can be moved along the entire longitudinal length of its respective slot 82 and is held in a fixed position by the fastener 86 occupying one of the notches formed within the slots 80 or 82. Thus, it can be seen that brackets 88 are capable of moving toward and away from the elongated center axis 26 thereby providing adjustment for the brackets 88 so as to accommodate various shoulder widths of patients 28. One bracket 88 is to be in contact with one shoulder of the patient 28 with the other bracket 88 to be in contact with the other shoulder of the patient 28.

Fixedly mounted on the upper surface of the plate 24 in a spaced apart manner are a pair of handles 90. The handles 90 are to be mounted on the plate 24 by means of conventional fasteners 92. It is the function of the handles 90 to facilitate grasping of the plate 24 and installing such into position onto the board 22 and also the subsequent removal of the plate 24 from the board 22 and the placing of such in an out-of-the-way position for storage.

With the patient 28 in position on the board 22 and the perineal post properly positioned as well as each bracket 88 in contact with the shoulders of the patient 28, it is necessary to move the plate 24 relative to the board 22 in the direction of arrow 48 a short distance to physically reposition or depress the shoulders of the patient 28 so that a lateral radiograph can be taken. In this position, the clavical of the shoulders will be displaced so as to not interfere with the taking of the radiograph. This displacing of the shoulders is shown in the dotted line positions of the patient within FIG. 1 of the drawings. This movement is to be caused by the use of a unidirectional force applying apparatus 94.

The force applying apparatus (a winch) 94 comprises a base 96 which is fixedly mounted by means of fasteners 98 onto the plate 24. Fixedly mounted onto the plate 96 and extending upward therefrom in a spaced apart manner are a pair of mounting flanges 100. Rotatably mounted within appropriate holes formed within the mounting flanges 100 is a shaft 102. Fixedly mounted on the shaft 102 on either side of the flanges 100 is a notched wheel 104. Each notched wheel 104 is to be in continuous engagement with a spring plate 106. The spring plate 106 is biased toward the notched wheels 104 by means of spring 108. The free outer end of the spring 108 is mounted against a flange plate 110 which is fixedly mounted by fasteners 98 onto the base 96. It is to be understood that the notched wheels 104, in conjunction with the spring plate 106, normally permit only rotation of the shaft 102 in a clockwise direction as shown in FIG. 2 of the drawings. Counterclockwise rotation of the shaft 102 can only occur upon movement of the spring plate 106 to disengage the notched wheels 104 compressing the spring 108.

Wound on th shaft 102 is a belt 112. The outer surface of the belt 112, which is wound on the shaft 102, is to be engageable with the forward edge of a biasing plate 114. Biasing plate 114 has mounted on the back end thereof a pin 116. Mounted about the pin 116 is a spring 118. The outer tip of the pin 116 rides within hole 120 formed within cross member 122. Cross member 122 is fixedly mounted between side members 124 and 126. The inner end of the side members 124 and 126 are mounted on handle 128. The biasing plate 114 is slidably movable between the side members 124 and 126 so that the outer end of the biasing plate 114 can dig into the strap 112 which is wound on the shaft 102.

The outer edge of the side plates 124 and 126 is pivotly mounted by pivot pin 130 to flanges 100. Manual pivoting motion of the handle 128 in the direction of the arrow 132 will result in turning clockwise of the portion of the strap 112 that is wound on shaft 102 since biasing plate 114 is in engagement therewith and is being carried along with the motion of the handle 128. Movement of the handle 128 in the direction reverse to arrow 132 will result in the biasing plate 114 to merely slip along the strap 112 wound on the shaft 102. However, the shaft 102 will remain in position as being held in that position by the spring plate 106 in engagement with the notched wheels 104. Thus, it can be seen that movement of the handle 128 in the direction of arrow 132 will cause the portion of the strap 112 not wound onto shaft 102 to be shortened. This portion of the strap 112 passes over a pin 134 mounted between the members 100 and also passes over roller 136 which is rotatably mounted on base plate 96.

The outer free end of the strap 112 is connected by a pin 138 which is fixedly mounted on the guide plate 140. The guide plate 140 includes an internal compartment 142. A rod 144 passes through a hole 146 formed within the guide plate 140 and is located within the internal compartment 142. Located about the portion of the rod 144 that is positioned within internal compartment 142 is a coil spring 148. The coil spring 148 is a compression spring that operates betwen a portion of the guide plate 140 and enlarged head 150 fixedly mounted on the end of the rod 144 which is located within the compartment 142.

The outer end of the rod 144 is fixedly attached to bifurcated joint member 152. Bifurcated joint member 152 is pivotly connected to hook member 154 by means of a pivot pin 156. The hook member 156 is to connect with the opening 32.

Thusly, as the handle 128 is pivoted in the direction of the arrow 132, the plate 24 is moved in the direction of arrows 158 relative to the board 22 or the board 68. Arrows 158 are in the same direction as arrow 48. This movement causes the brackets 88 to apply pressure against the shoulders, depressing such of the patient 28. As force is applied onto the shoulders, it is important that the technician not apply too much force which may result in injury to the patient 28. In order to assist the technician in knowing the amount of force that is being applied, there is incorporated within the plate 24 a series of closely spaced apart holes 160. There may be inserted a series of lines (as shown in the drawings) directly alongside holes 160. This series of lines is intended to assist the technician in determining the amount of force being applied. There may also be used numericolor alphabetical indicia (not shown).

The technician is able to observe the forward most end of the guide plate 140 with respect with the holes 160 (and series of lines) prior to the applying of force to the shoulders of the patient 28. As force is applied, guide plate 140 will move along rod 144 compressing the spring 148 which will supply the force being applied to the shoulders of the patient. The technician visually observes the new position of the guide plate 140 with respect to a hole 160 and compares such to the hole 160 where the initial application of force occurred. The technician is then able to make a determination that a certain amount of force has been applied if the guide plate 140 has moved one hole, two holes or three holes 160 from the initial application of force.

Referring particularly to FIG. 10 of the drawings, at times, a patient 162 may not be located on an elongated board such as board 22 or board 68. In such an instance, the patient 162 will be located merely on a table. It may be deemed to be potentially injurious to move the patient 162, but it is still necessary to take an X-ray of the cervical region of th spine of the patient 162. In such an instance, a modified portion of a board 164 can be utilized which is basically a shortened version of the board 22. The modified version 164 includes hand holds 166 and a strip plate 168 which is basically identical to strip plate 38. The strip plate 168 includes keyhole slots 170. The strip plate 168 is primarily fixedly mounted on forward protrusion 172 of the board 164.

The board 164 is to be carefully slipped under the patient 162 as the patient is lying on the table (not shown). This slipping of the board 164 in position is such that the strip plate 168 will extend within the crotch area of the patient 162. At such time the perineal post assembly, which has been previously described, will be connected with a pair of the keyhole slots 170. The plate 24 will then be mounted onto the side edges of the board 164 in the same manner that the plate 24 is mounted on the boards 22 or 68. The hook 154 is to engage with the opening 174 formed within the board 164.

What is claimed is:

1. A body positioning apparatus for repositioning the human shoulder to facilitate the taking of radiographs of the cervical region of a prone patient comprising:

an elongated substantially planar board having an elongated center axis, said board having an upper end and a pair of side edges, whereby the head of the patient is adapted to be located at said upper end and the shoulders of the patient to be located directly adjacent said upper end with the spine of the patient in substantial alignment with said elongated center axis;

a plate connected by sliding means to said board at said upper end, said sliding means being mounted on said side edges, said sliding means permitting relative movement between said plate and said board along said elongated center axis, said plate overlying said upper end of said board;

shoulder engaging means mounted on said plate, said shoulder engaging means to contact the shoulders of the patient;

movement means for causing movement of said plate relative to said board causing the applying of pressure onto said shoulders of the patient; and fixing means mounted on said board, said fixing means to engage with the torso of the patient to prevent movement of such during depressing of the shoulders by said shoulder engaging means.

2. The body positioning apparatus as defined in claim 1 wherein:

said relative movement between said plate and said board being only along said longitudinal center axis.

3. The body positioning apparatus as defined in claim 2 wherein:

said sliding means being movably mounted on said plate in a direction substantially transverse to said elongated center axis, said sliding means to be adjustable to facilitate connection of said plate to different widths of said board.

4. The body positioning apparatus as defined in claim 1 wherein:

said shoulder engaging means comprising a pair of spaced apart brackets, each said bracket protruding outward from said plate, each said bracket being individually adjustable in respect to said plate in a direction substantially transverse to said elongated center axis.

5. The body positioning apparatus as defined in claim 1 wherein:

said fixing means comprising a perineal post, said perineal post being adapted to be in continuous contact with the perineal portion of the body of the patient.

6. The body positioning apparatus as defined in claim 5 wherein:

said perineal post being adjustably mounted to be located at any one of a plurality of different positions on said board.

7. The body positioning apparatus as defined in claim 1 wherein:

said movement means being operable to move said plate at a slow steady rate in respect to said board, said movement means being selectably disengageable at any desired instant.

8. A body positioning apparatus for repositioning the human shoulder to facilitate the taking of radiographs of the cervical region of a prone patient comprising:

an elongated substantially planar board having an elongated center axis, said board having an upper end, whereby the head of the patient is adapted to be located at said upper end and the shoulders of the patient to be located directly adjacent said upper end with the spine of the patient in substantial alignment with said elongated center axis;

a plate connected by sliding means to said board at said upper end, said sliding means permitting relative movement between said plate and said board along said elongated center axis;

shoulder engaging means mounted on said plate, said shoulder engaging means to contact the shoulders of the patient;

movement means for causing movement of said plate relative to said board causing the applying of pressure onto said shoulders of the patient;

fixing means mounted on said board, said fixing means to engage with the torso of the patient to prevent movement of such during depressing of the shoulders by said shoulder engaging means;

said movement means being operable to move said plate at a slow steady rate in respect to said board, said movement means being selectably disengageable at any desired instant; and said movement means comprising a manually operated winch, said winch being mounted on said plate, said winch being connected to a strap, said strap being movable during operation of said winch, said strap having an outer end, said outer end being connected to said board.

9. The body positioning apparatus as defined in claim 8 wherein:

said strap being directly connected to a spring assembly, said spring assembly being directly connected to said board, said spring assembly to stretch as force is applied through said shoulder engaging means to the shoulders of the patient.

10. The body positioning apparatus as defined in claim 9 wherein:

said plate including force determining means, said force determining means being visually observable by the operator of said body positioning apparatus to determine the amount of force being applied to the shoulders of the patient.

11. The body positioning apparatus as defined in claim 10 wherein:

said force determining means comprising a series of spaced apart holes formed within said plate, said spaced apart holes being located in close proximity to said spring assembly, as said spring assembly is stretched said spring assembly is moved from one position directly adjacent one said hole to another position directly adjacent another said hole.

12. A body positioning apparatus for repositioning the human shoulder to facilitate the taking of radiographs of the cervical region of a prone patient comprising:

an elongated substantially planar board having an elongated center axis, said board having an upper end, whereby the head of the patient is adapted to be located at said upper end and the shoulders of the patient to be located directly adjacent said upper end with the spine of the patient in substantial alignment with said elongated center axis;

a plate connected by sliding means to said board at said upper end, said sliding means permitting relative movement between said plate and said board along said elongated center axis;

shoulder engaging means mounted on said plate, said shoulder engaging means to contact the shoulders of the patient;

movement means for causing movement of said plate relative to said board causing the applying of pressure onto said shoulder of the patient;

fixing means mounted on said board, said fixing means to engage with the torso of the patient to prevent movement of such during depressing of the shoulders by said shoulder engaging means; and said plate including force determining means, said force determining means being visually observable by the operator of said body positioning apparatus to determine the amount of force being applied to the shoulders of the patient.

* * * * *